US006773890B2

(12) United States Patent
Goldenring et al.

(10) Patent No.: US 6,773,890 B2
(45) Date of Patent: Aug. 10, 2004

(54) SCREEN FOR RISK FOR GASTRIC ADENOCARCINOMA

(75) Inventors: James R. Goldenring, Nashville, TN (US); P. Henry Schmidt, Augusta, GA (US); Jeffrey R. Lee, Martinez, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 0 days.

(21) Appl. No.: 10/060,113

(22) Filed: Jan. 29, 2002

(65) Prior Publication Data

US 2002/0187487 A1 Dec. 12, 2002

Related U.S. Application Data

(62) Division of application No. 09/164,954, filed on Oct. 1, 1998, now Pat. No. 6,372,439.

(51) Int. Cl.$^7$ .......................... G01N 33/53; C12N 1/00; C07K 16/00

(52) U.S. Cl. ...................... 435/7.1; 435/810; 530/387.1

(58) Field of Search ........................ 530/387.1; 435/7.1, 435/810

(56) References Cited

U.S. PATENT DOCUMENTS 5,567,594 A   10/1996   Calenoff
5,783,416 A    7/1998   Thim et al.

FOREIGN PATENT DOCUMENTS

DE    196 29 938 C1    11/1997
WO    WO 96/15456 A1    5/1996

OTHER PUBLICATIONS

Hirose et al, (Gann, 1976, 67:(3):355–364).*
Suzuki et al (I To Cho, 1980, 15:*
Tomado (Fukoka Act Med., 1983, 74:366–382).*
Ahnen, et al., "The ulceration–associated cell lineage (UACL) reiterates the Brunner's gland differentiation programme but acquires the proliferative organization of the gastric gland," *J. Pathol.* 173: 317–326 (1994).
Alison, et al., "Experimental ulceration leads to sequential expression of spasmolytic polypeptide, intestinal trefoil factor, epidermal growth factor and transforming growth factor alpha mRNAs in rat stomach," *J. Pathol.* 175: 405–414 (1995).
Babyatsky, et al., "Oral trefoil peptides protect against ethanol– and indomethacin–induced gastric injury in rats," *Gastroenterology* 110: 489–497 (1996).
Beck, et al., "Cloning of contiguous genomic fragments from human chromosome 21 harbouring three trefoil peptide genes," *Hum Genet* 98(2): 233–235 (1996).

Bluth, et al., "Immunolocalization of transforming growth factor–alpha in normal and diseased human gastric mucosa," *Hum. Pathol.* 26: 1333–1340 (1995).
Correa, P., "A human model of gastric carcinogenesis," *Cancer Res.* 48: 3554–3560 (1988).
Dempsey, et al., "Possible role of transforming growth factor alpha in the pathogenesis of Menetrier's disease: supportive evidence from humans and transgenic mice," *Gastroenterology* 103: 1950–1963 (1992).
DHI Conference on H pylori, *Gastroenterolgy* 113:S4–S8 (1997).
Dixon, et al., "Classification and grading of gastritis. The updated Sydney System." *Am. J. Surg. Pathol.* 20:1161–1181 (1996).
Elia, et al., "The production and characterization of a new monoclonal antibody to the trefoil peptide human spasmolytic polypeptide," *Histochem. J.* 26: 644–647 (1994).
Filipe, et al., "Intestinal metaplasia types and the risk of gastric cancer: a cohort study in Slovenia," *Int. J. Cancer* 57: 324–329 (1994).
Fox, et al., "Hypertrophic gastropathy in Helicobacter felis–infected wild–type C57BL/6 mice and p53 hemizygous transgenic mice," *Gastroenterology* 110: 155–166 (1996).
Goldenring, et al., "Expression of trefoil peptides in the gastric mucosa of transgenic mice overexpressing transforming growth factor–alpha," *Growth Factor* 13(1–2): 111–119 (1996).
Haggitt, "Barrett's esophagus, dysplasia, and adenocarcinoma," *Hum. Pathol.* 25: 982–993 (1994).
Hanby, et al., The expression of the trefoil peptides pS2 and Human spasmolytic polypeptide (hSP) in 'Gastric Metaplasia' of the proximal duodendum: implications for the nature of 'Gastric Metaplasia', *J. Path.* 169:355–360 (1993).

(List continued on next page.)

*Primary Examiner*—Susan Ungar
(74) *Attorney, Agent, or Firm*—Kilpatrick Stockton LLP; Charles W. Calkins; Cynthia B. Rothschild

(57) ABSTRACT

It has been determined that a specific metaplastic lineage that contains immunoreactivity for a trefoil polypeptide, spasmolytic peptide, is associated with and gives rise to the vast majority of human adenocarcinomas. The identification of this Spasmolytic Polypeptide Expressing Metaplasia (SPEM) is a major factor for grading of biopsies of the stomach to assess risk for gastric cancer. It also forms the basis of a method for serological screening for those at risk for gastric cancer. In a preferred embodiment, antibodies to spasmolytic peptide (hSP) are used in immunostaining of biopsies of gastric tissue obtained by endoscopy for grading biopsies. Those patients having these cells, characterized by a morphology more typical of a type of cell present normally in the intestine and not stomach, Brunner's gland cells, are at risk of developing adenocarcinoma. Since these cells express hSP, antibodies or nucleic acid probes hybridizing to mRNA encoding hSP, can be used for rapid detection of the cells in tissue biopsies. The antibodies can also be used in serological tests for screening and following patients at risk for gastric cancer. In combination with evidence of previous or present invention with *H. pylori*, the tests are predictive of the likelihood of developing adenocarcinoma.

9 Claims, No Drawings

OTHER PUBLICATIONS

Itoh, et al., "cDNA cloning of rat pS2 peptide and expression of trefoil peptides in acetic acid–induced colitis," *Biochem. J.* 318(Pt 3): 939–944 (1996).

Konturek, et al., "Activation of genes for spasmolytic peptide, transforming growth factor alpha and for cyclooxygenase (COX)–1 and COX–2 during gastric adaptation to aspirin damage in rats," *Aliment. Pharmacol. Ther.* 12(8): 767–777 (1998).

Konturek, et al., "Role of spasmolytic polypeptide in healing of stress–induced gastric lesions in rats," *Regul. Pept.* 68(1): 71–79 (1997).

Lee, et al., "A small animal model of human Helicobacter pylori active chronic gastritis," *Gastroenterology* 99: 1315–1323 (1990).

Lefebvre, et al., "Gastric mucosa abnormalities and tumorigenesis in mice lacking the pS2 trefoil protein," *Science* 274: 259–262 (1996).

Majumdar, et al., "Localization and significance of pp55, a gastric mucosal membrane protein with tyrosine kinase activity," *Am. J. Physiol.* 274(5, 1): G863–870 (1998).

McKenzie, et al., "Pancreatic spasmolytic polypeptide protects the gastric mucosa but does not inhibit acid secretion or motility," *Am. J. Physiol.* 273: G112–G117 (1997).

Miros, et al., "Only patients with dysplasia progress to adenocarcinoma in Barrett's oesophagus," *Gut* 32: 1441–1446 (1991).

Mobley, "Helicobacter pylori factors associated with disease development," *Gastronenterology* 113: S21–S28 (1997).

Modlin, et al., Ulcer–induced alterations in cell phenotype and matrix and growth factor expression, *Eur. J. Gastro. Hepatol.* S59–S67 (1993).

Molloy, et al., Relation between gastric cancer and previous peptic ulcer disease, *Gut* 40:247–252 (1997).

Nomura, et al., "Helicobacter pylori infection and gastric carcinoma among Japanese Americans in Hawaii," *New Eng. J. Med.* 325: 1132–1136 (1991).

Parsonnet, et al., "Helicobacter pylori infection and the risk of gastric carcinoma," *New Eng. J. Med.* 325: 1127–1131 (1991).

Peura, "The Report of the Digestive Health Initiative[SM] International Update Conference on Helicobacter pylori," *Gastroenterology* 113: S4–S8 (1997).

Podolsky, et al., "Identification of human intestinal trefoil factor. Goblet cell–specific expression of a peptide targeted for apical secretion," *J. Biol. Chem.* 268: 6694–6702 (1993).

Polshakov, et al., "NMR–based structural studies of the pNR–2/pS2 single domain trefoil peptide. Similarities to porcine spasmolytic peptide and evidence for a monomeric structure," *Eur. J. Biochem.* 233(3): 847–855 (1995).

Reid, et al., "Flow–cytometric and histological progression to malignancy in Barrett's esophagus: prospective endoscopic surveillance of a cohort," *Gastroenterology* 102: 1212–1219 (1992).

Robertson, et al., "Values of endoscopic surveillance in the detection of neoplastic change in Barrett's oesophagus," *Br. J. Surg.* 75: 760–763 (1988).

Schmidt, et al., "Association of an aberrant spasmolytic peptide—expressing cell lineage with gastric adenocarcinoma in humans," *Gastroenterology* 114:A673 (1998).

Schmitt, et al., "A third P–domain peptide gene (TFF3), human intestinal trefoil factor, maps to 21q22.3," *Cytogenet. Cell Genet.* 72(4): 299–302 (1996).

Seitz, et al., "Breast cancer–associated protein pS2 expression in tumors of the biliary tract," *Am. J. Gastroenterol.* 86(10): 1491–1494 (1991).

Tanaka, et al., "Human spasmolytic polypeptide decreases proton permeation through gastric muscus in vivo and in vitro," *Am. J. Physiol.* 272(6): G1473–1480 (1997).

Tannock, et al., "The Basic Science of Oncology" $2^{nd}$ ed., McGraw–Hill, New York, pp. 201–203 (1992).

Theisinger, et al., "Expression of the breast cancer associated gene PS2 and the pancreatic spasmolytic polypeptide gene (hSP) in diffuse type stomach carcinoma," *Eur. J. Cancer* 27:770–773 (1991).

Thim, L., "A new family of growth factor–like peptides," *FEBS Lett.* 250: 85–90 (1989).

Tockman, et al., Considerations in bringing a cancer biomarker to clinical application, *Cancer Res.* 52:2711s–2718s (1997).

Tomassetto, et al., "hSP, the domain–duplicated homolog of pS2 protein, is co–expressed with pS2 in stomach but not in breast carcinoma," *EMBO J.* 9(2): 407–414 (1990).

Wang, et al., "Mice lacking secretory phosholipase A2 show altered apoptosis and differentiation with Helicobacter felis infection," *Gastroenterology* 114: 675–689 (1998).

Wright, et al., "Induction of a novel epidermal growth factor–secreting cell lineage by mucosal ulceration in human gastrointestinal stem cells," *Nature* 343: 82–85 (1990).

PCT International Search Report corresponding to PCT/ application from PCT/US98/20820 ("Screen for Risk for Gastric Adenocarcinoma").

Josh, V. et al.; Aberrant Mucous Neck Cell Lineages Associated with Fundic H. Pylori Gastritis; Gastroenterology 112: A 163, 1997.

* cited by examiner

SCREEN FOR RISK FOR GASTRIC ADENOCARCINOMA

This application is a divisional of U.S. patent application Ser. No. 09/164,954, filed Oct. 1, 1998, which issued on Apr. 16, 2002, as U.S. Pat. No. 6,372,439.

The United States government has certain rights in this invention by virtue of a grant from the National Institutes of Health NIDDKD to James R. Goldenring.

BACKGROUND OF THE INVENTION

Gastric cancer worldwide is the second highest cause of death from cancer. While rates of gastric cancer have been decreasing in the United States, gastric cancer prevalence remains high in other parts of the world, especially in Asia. Presently, patients in endemic regions for gastric cancer, especially Japan and China, undergo screening by upper endoscopy. There is no alternative at present for discovery of early cancer other than by endoscopy. Grading of these endoscopies is based solely on hematoxylin and eosin staining. There are no prognostic markers that could indicate those at risk for future cancer development. Therefore, while biopsies can reveal early gastric cancers, patients in high risk regions who are initially negative by endoscopy must be followed with endoscopies in rule out future developments.

The epidemiological association between chronic *H. pylori* infection and gastric carcinoma is now well established, such that the Working Group Meeting of the International Agency for Research on Cancer with the World Health Organization recently classified *Helicobacter pylori* as a group 1 human gastric carcinogen (Peura, D. A. *Gatroenterology*. 113, S4–S8 (1997)). Parsonnet and colleagues reported that 84% of patients with gastric cancer had serum antibodies against *H. pylori*, as opposed to 66% of uninfected matched controls (Parsonnet, et al. *New Eng. J. Med.* 325, 1127–1131 (1991)). *H. pylori* infection induces a chronic gastritis progressing to atrophic gastritis, foveolar hyperplasia and intestinal metaplasia (Mobley, H. T. L. *Gastronenterology*. 113, S21–S28 (1997)). Recent studies have indicated that chronic gastritis associated with *Helicobacter pylori* contributes to the development of gastric adenocarcinoma (Peura, D. A. *Gatroenterology*. 113, S4–S8 (1997); Parsonnet, et al. *New Eng. J. Med.* 325, 1127–1131 (1991); Forman et al. *Br. J. Med.* 302, 1302–1305 (1991); Nomura, et al. *New Eng. J. Med.* 325, 1132–1136 (1991)). Nevertheless, the mechanism of progression from chronic gastritis to malignant disease remains unclear, and the relationship of intestinal metaplasia, *H. pylori* infection and the development of cancer continues to be controversial. Moreover, while an association between gastric cancer and infection with *H. pylori* has recently been established, the cell of origin for gastric adenocarcinoma is controversial. This does not establish a mechanism between the bacteria and the cancer, and provides little or no guidance for correlating treatment of, or risk associated with, *H. pylori* as it relates to development of gastric cancer.

It is therefore an object of the present invention to provide screening methods for early gastric cancer.

It is a further object of the present invention to provide means for assessing the degree of early gastric cancer and for screening and following patients at risk for gastric cancer.

It is a still further object of the present invention to provide means for serological testing for patients at risk of gastric cancer.

SUMMARY OF THE INVENTION

It has been determined that a specific metaplastic lineage that contains immunoreactivity for a trefoil polypeptide, spasmolytic peptide, is associated with and gives rise to the vast majority of human adenocarcinomas. The identification of this Spasmolytic Polypeptide Expressing Metaplasia (SPEM) is a major factor for grading of biopsies of the stomach to assess risk for gastric cancer. It also forms the basis of a method for serological screening for those at risk for gastric cancer. In a preferred embodiment, antibodies to spasmolytic peptide (hSP) are used in immunostaining of biopsies of gastric tissue obtained by endoscopy for grading biopsies. Those patients having these cells, characterized by a morphology more typical of a type of cell present normally in the intestine and not stomach, Brunner's gland cells, are at risk of developing adenocarcinoma. Since these cells express hSP, antibodies or nucleic acid probes hybridizing to mRNA encoding hSP, can be used for rapid detection of the cells in tissue biopsies. The antibodies can also be used in serological tests for screening and following patients at risk for gastric cancer. In combination with evidence of previous or present invention with *H. pylori*, the tests are predictive of the likelihood of developing adenocarcinoma.

DETAILED DESCRIPTION OF THE INVENTION

Metaplastic cell lineages arising in response to chronic injury are precursors for the evolution of dysplasia and adenocarcinoma. This sequence is well characterized in the case of the Barrett's epithelium, a columnar specialized intestinal metaplasia in the distal esophagus of patients with esophageal reflux (Haggitt, R. C. *Hum. Pathol.* 25, 982–993 (1994)). While a subtype of intestinal metaplasia has been associated with gastric adenocarcinoma (Dixon, et al. *Am. J. Surg. Pathol.* 20, 1161–1181 (1996); Filipe et al. *Int. J. Cancer.* 57, 324–329 (1994)); Correa, P. *Cancer Res.* 48, 3554–3560 (1988)), the link between these lineages and the evolution of gastric adenocarcinoma has not been clear. It has now been determined that there is an association between SPEM, detectable in biopsies based on the presence of cells having a morphology similar to Brunner's gland cells, and adenocarcinoma. Although normal cells in the stomach, such as mucus neck cells, express hSP, these cells are not predictive of adenocarcinoma.

I. Methods and Reagents for Screening

A. Histology of the Gastric Tissues

Presently, gastric mucosal biopsies are fixed in formalin and embedded in paraffin. Mictrotome sections of tissues are then stained with hematoxylin and eosin. These stained slides are examined for loss of parietal cells (oxyntic atrophy), ulceration, inflammatory infiltrates, and alterations in cell lineages including increased numbers of surface mucous cells (foveolar hyperphasia), the presence of goblet cells (intestinal metaplasia), as well as dysplasia and adenocarcinoma. Dysplasia and adenocarcinoma are judged by changes in nuclear morphology, loss of cytoplasmic space, loss of polarity and invasion of submucosa or vasculature. Brunner's glands are not present in the normal stomach but can be observed in the duodenum.

B. Markers of SPEM

Small peptides displaying a cysteine-rich module (termed P-domain or trefoil motif) form a group of peptides, including BCEI, expressed from the pS2 gene; hITF, expressed from the TFF3 gene; and hSP, expressed from the SML1 gene. These peptides are abundantly expressed at mucosal surfaces of specific tissues and are associated with the maintenance of surface integrity (Schmitt, et al., *Cytogenet. Cell Genet.* 72(4), 299–302 (1996)). Human spasmolytic peptide (hSP) was identified by Romasetto, et al., EMBO J., 9(2), 407–414 (1990), based on homology to pancreatic spasmolytic polypeptide, sequenced and determined to be separately encoded on the genome from pS2. The gene sequence and amino acid sequences of hSP can be obtained from GenBank, accession number 1477545. Both are present in normal stomach epithelium. The patterns and timing of the expression of the trefoil peptides are different from each other. It is thought that S2 plays an important role in the proliferation of intestinal epithelial cells during the acute phase of mucosal ulceration, whereas ITF may be involved in differentiation of the cells, particularly to form goblet cells, during the recovery phase of acute colitis (Itoh, et al., *Biochem. J.* 318(Pt 3), 939–944 (1996)). Immunostaining for SP in the intact mucosa has been determined to be confined to the mucous neck cells, but following exposure to stress it was significantly enhanced and occurred also in the cells of the basal region of gastric glands, as reported by Konturek, et al., *Regul. Pept.* 68(1), 71–79 (1997). Konturek, et al. (1997) proposed that SP plays an important role in healing of stress-induced gastric lesions, possibly by the acceleration of the mucosal repair, the enhancement of mucosal blood flow and the inhibition of gastric secretion.

It has now been determined that SP is a marker of metaplastic cells having a morphology similar to those of Brunner's gland cells. These cells can be identified by histological examination. However, the identification of SPEM with spasmolytic peptide immunostaining is easier, more sensitive and rapid. Therefore, detection of metaplastic cells expressing SP provides a means for identification of those at risk who would need further follow-up. Furthermore, since the SPEM lineage is often extensive, quantitation of serum spasmolytic polypeptide levels by either radioimmunoassay or ELISA should be useful to stratify patients at risk and provide a serological method for identifying and following patients at risk for developing adenocarcinoma.

SPEM can be detected using antibodies or antibody fragments prepared by standard techniques. The studies described in the examples were performed with a mouse monoclonal IgM anti-human spasmolytic polypeptide developed by Drs. Richard Poulsom and Nicholas Wright at the Imperial Cancer Research Fund, London, UK. Antibodies specifically directed towards utility in RIA and ELISA have also been developed. Either monoclonal or polyclonal antibodies can be used. Antibodies can be labelled using any detectable marker, including radiolabels, fluorescent labels, dyes, enzyme-chromogenic substrate systems, and other means commercially available.

SPEM can also be detected using nucleic acid probes which hybridize under standard hybridization conditions, as described for example, by Maniatis, et al. Molecular Cloning: A Laboratory Manual (Cold Spring Harbor Laboratory), to mRNA encoding SP. These can be labeled using standard labelling techniques for detection of bound nucleic acid Alternatively, or in addition, other markers of these cells can be used to screen for the presence of SPEM in gastric tissue biopsies.

For serological assay of SP, serum would be obtained from fasting patients. SP levels would be determined using either radioimmunoassay or enzyme-linked immunoassay. A standard curve would be used for known amounts of recombinant SP (Lars Thimm, Novartis Corporation). Patients with elevated levels of SP in serum would be investigated for the presence of SPEM by endoscopy. Alternatively, patients with elevated serum SP and documented SPEM could be followed following treatment of *H. pylori* by serial serum determinations of SP.

C. Detection of *H. pylori* Infection

Since *H. pylori* is known to be associated with an increased incidence of adenocarcinoma of the stomach, efficacy of screening can be further enhanced by testing for previous or present *H. pylori* infection. *H. pylori* infection would be determined by either CLO test at the time of biopsy or *H. pylori* serology with the same sample used for SP determination.

II. Patients to be Screened and Screening Procedures

SP detection, such as immunohistochemistry, can be used to determine the presence of SPEM in endoscopic biopsies as well as brushings obtained either through endoscopy or blind per oral intubation.

As noted above, gastric cancer screening, especially in Asian countries, is a major focus for clinical care. Presently, the only impact of medicine on gastric cancer is through early detection of low grade tumors and early resection for cure. High grade tumors have uniformly dismal prognosis with median survival less than one year. No significant effect of adjuvant chemotherapy has been noted. The addition of spasmolytic polypeptide immunostaining of biopsies and the identification of SPEM provides a means for identifying those at risk for developing cancer in the future. Similarly, the use of spasmolytic peptide serology should provide a blood test for identification of those at risk. Thus, the use of spasmolytic polypeptide immunostaining could significantly decrease the number of screening endoscopies, focus screening endoscopies, and, through serology testing, facilitate screening of large population a risk in Asia and other countries with high cancer incidence.

The present invention will be further understood by reference to the following non-limiting examples.

Background

Wang and colleagues examined the influences of chronic Helicobacter gastritis using *Helicobacter felis* to infect the gastric epithelium of C57BL/6 mice (Wang, et al. *Gastroenterology* 114, 675–689 (1998)). Infection with *H. felis* produced a chronic gastritis with pathologic features similar to human infection with *H. pylori* including marked loss of parietal and chief cell populations, in addition to elaboration of an aberrant mucous cell lineage (Lee, et al. *Gastroenterology* 99, 1315–1323 (1990); Fox, et al., *Gastroenterology* 110, 155–166(1996)). Wang, et al (1998) reported that an aberrant metaplastic cell lineage with morphological characteristics similar to Brunner's glands of the duodenum develops in the fundic mucosa of mice infected with *H. felis*. This metaplastic lineage expresses the trefoil peptide spasmolytic polypeptide (SP). This expanded lineage stained with antibodies against spasmolytic polypeptide (SP), a trefoil peptide secreted from mucous neck cells in the normal fundic mucosa (Wang, et al. (1998); Thim, L. FEBS Lett. 250, 85–90 (1989)). Importantly, the *H. felis*-induced SP-expressing metaplastic (SPEM) lineage did not show morphological characteristics of mucous neck cells, but rather demonstrated morphology more reminiscent of Brunner's glands of the duodenum (Wang (1998)).

Hypothesis

Given the results in mice, studies were designed to investigate whether *H. pylori* infection would induce a similar aberrant SP-expressing lineage in human fundic mucosa. Given the epidemiological association of *Helicobacter sp.* infection with gastric cancer, it was hypothesized that this SP-expressing metaplastic (SPEM) lineage may represent a precursor to or appear commensurate with gastric adenocarcinoma.

Summary of Results

The results of these studies showed that the SPEM lineage was present in 65% of fundic biopsies from patients with fundic *H. pylori*-associated gastritis, but was absent in biopsies of fundic mucosa from patients without *H. pylori* infection. In a review of archival samples from 22 resected gastric adenocarcinomas, the SPEM lineage was found in 91% of cases, typically located in mucosa adjacent to the carcinoma or areas of dysplasia. Importantly, 56% of samples showed SP immunoreactivity within dysplastic cells. These data indicate not only a strong association between the SPEM lineage and gastric adenocarcinoma, but that SPEM cells represent the metaplastic lineage responsible for development of this tumor in patients with *H. pylori*.

EXAMPLE 1

Detection of SP levels in gastric fundic biopsies.

Ten fundic biopsies from *H. pylori* negative patients and 17 biopsies from patients with *H. pylori* colonization in the fundus were examined. All biopsies demonstrated H/K-ATPase-immunostaining parietal cells and contained no gastrin-immunoreactive cells, confirming the authenticity of fundic mucosal biopsies. In all of the *H. pylori*-infected biopsies specimens, the presence of *H. pylori* was confirmed by Giemsa staining of tissue sections. The histological characteristics of these biopsies are summarized in Table I.

TABLE I

Histological analysis of fundic biopsies from *H. pylori* (Hp) negative and *H. pylori* positive patients.

|  | HP Negative | | HP Positive | |
| --- | --- | --- | --- | --- |
|  | Absent | Present | Absent | Present |
| Foveolar hyperplasia | 10 | 0 | 4 | 13 |
| Oxyntic atrophy | 10 | 0 | 6 | 11 |
| Mononuclear infiltrates | 8 | 2 | 1 | 16* |
| SPEM | 10 | 0 | 6 | 11 |

Foveolar hyperplasia was assessed in sections stained for pS2 as the presence of surface cells in greater than 25% of the gland length. Oxyntic atrophy was assessed in sections stained for H/K-ATPase as a decrease in parietal cell density to less than half the gland length. Mononuclear infiltrates were assessed in H&E stains.
*3 of 16 *H. pylori* (Hp) positive patients demonstrated organized lymphoid aggregates. SPEM was assessed in sections stained for hSP.

Gastric fundic biopsies were stained for SP. 10 $\mu$m sections from paraffin-embedded biopsies of fundic mucosa from *H. pylori* uninfected and *H. pylori* infected patients were stained for hSP with a monoclonal murine anti-HSP Elia, et al. *Histochem. J.* 26, 644–647 (1994)). Dewaxed paraffin sections were blocked with 5% goat serum in phosphate buffered saline and then incubated with anti-hSP (1:50) for one hour at room temperature. Indirect immunohistochemical detection was then performed through incubation with biotinylated anti-mouse IgG, streptavidin-conjugated alkaline phosphatase and finally Vector Red chromogen substrate (Vector-Laboratories, Burlingame, Calif.). For confirmation of the veracity of biopsies as fundic mucosa, serial sections were also stained with monoclonal antibodies against the HIK-ATPase (1:5000, the gift of Dr. Adam Smolka, Medical University of South Carolina, a marker of parietal cells) and gastrin (undiluted, Zymed, a marker of antral G-cells).

The presence of *H. pylori* was confirmed in all biopsies with Giemsa staining. All biopsies demonstrated immunoreactive parietal cells without the presence of G-cells). In non-infected patients, staining was confined to normal appearing mucous neck cells. In *H pylori*-infected patients, nodular aggregates of hSP-staining cells with the characteristics of Brunner's gland cells (SPEM) were observed in 65% of biopsies. No SPEM was observed in fundic biopsies from non-infected patients.

In non-infected patients, fundic biopsies demonstrated only normal appearing SP-immunoreactive mucous neck cells. In contrast, 65% of biopsies from *H. pylori* infected biopsies exhibited aberrant hSP-immunoreactive SPEM cells. The lineage showed a morphology more characteristic of Brunner's gland cells. Most cells were present as nodular formations in the deeper portions of the metaplastic glands. Foveolar hyperplasia was present in 70% of *H. pylori* infected biopsies (Table I). Significant mononuclear infiltrate was present in 95% of biopsies with 18% of the biopsies demonstrating organized lymphoid aggregates. These results indicated that the SPEM lineage was present in the fundic mucosa of many patients with *H. pylori*-associated fundic gastritis.

EXAMPLE 2

Association of SPEM with Gastric Adenocarcinomas.

Since chronic *H. pylori* infection is associated with the development of adenocarcinoma, archived tissues from resected gastric adenocarcinomas in patients were examined. All of the resections were for tumors of the fundus or fundal/antral border.

Ten $\mu$m sections of paraffin-embedded mucosa from regions adjacent to gross adenocarcinoma were examined for immunostaining with hSP antibodies as described above. Prominent regions of SPEM were observed in mucosa underlying regions of foveolar hyperplasia. The lineage was always observed near the bases of glands. As noted in the biopsies, the SPEM cells were large with extensive numbers of immunoreactive granules. In an adjacent region, hSP staining of normal-appearing mucous neck cells was observed. Parietal cells were also observed in these sections. Adjacent sections were stained with anti-PSTI (1:200) with staining as described above except that sections underwent retrieval using citrate buffer in a microwave and horseradish peroxidase-conjugated secondary antibodies were used for detection with diaminobenzidine chromogen. While distinct PSTI immunoreactive mucous neck cells were observed within the mucosa, the SPEM lineage cells at the right side of the section showed no PSTI immunoreactivity. Adjacent sections were also stained with anti-PS2 (1:50) as described above. While pS2 immunostaining was observed in regions of surface cell foveolar hyperplasia, SPEM cells did not stain for pS2. Toluidine blue staining of a 0.5 $\mu$m section of glutaraldehyde fixed tissue from a resection specimen demonstrates the numerous granules in SPEM cells. Note the presence of residual parietal cells in some SPEM-containing glands, confirming the presence of the lineage in fundic mucosa. Electron microscopic examination demonstrates the presence of multiple mucous granules within the SPEM cells along with the characteristic expanded apical membrane surface without microvilli.

In summary, twenty patients (91%) demonstrated the SPEM lineage within their resection specimens. No evidence of the lineage was observed in two patients with diffuse infiltrating adenocarcinoma. In most specimens, a prominent homogeneous cell population expressing hSP was noted dominating greater than half the lower length of the fundic glands. These SPEM cells possessed an abundance of cytoplasmic mucin granules and a wide apical surface.

Branching of SPEM-containing glands was observed in many specimens. Most glands displayed varying degrees of oxyntic cell atrophy, however there was more variability in expansion of the surface cell compartment, with 68% of patients having foveolar hyperplasia. Normal mucous neck cell staining with hSP and parietal cells were observed in regions adjacent to SPEM-containing regions. Goblet cell-containing intestinal metaplasia was only observed in 10% of specimens.

Resection specimens were stained with several lineage-specific markers to characterize the origin of the SPEM lineage more completely. Increased expression of TGFα has been noted previously in foveolar cells of patients with Menetrier's disease and hypertrophic lymphocytic gastritis (Dempsey, et al. *Gastroenterology*. 103, 1950–1963 (1992); Bluth, et al. *Hum. Pathol*. 26, 1333–1340 (1995)). However, clear overexpression of TGFα in the foveolar regions of the mucosa adjacent to tumor was not observed. In addition, the SPEM lineage did not stain with antibodies against TGFα. In all cases, there was no evidence of enterochromaffin-like (ECL) cell hyperplasia, although scattered chromogranin A immunoreactive cells were observed. The SPEM lineage did not stain with antibodies against chromogranin A. While antibodies against pancreatic secretory trypsin inhibitor (PSTI) did stain scattered normal appearing mucous neck cells (McKenzie, et al. *Am. J. Physiol*. 273, G112–G1117 (1997)), no staining of the lineage was observed. While antibodies against the trefoil peptide pS2 did stain surface mucous cells in areas of foveolar hyperplasia, no staining was observed in the SPEM lineage. Previous investigations have suggested that Intestinal Trefoil Factor (ITF), which is absent from the normal gastric mucosa, is unregulated following injury (Podolsky, et al. *J. Biol. Chem*. 268, 6694–6702 (1993); Alison, et al. *J. Pathol*. 175, 405–414 (1995)). While occasional cells expressing ITF mRNA could be identified in regions of intestinal metaplasia, no ITF expression could be documented in the SPEM lineage. Finally, examination of SPEM in both thick and thin plastic sections demonstrated the presence of abundant mucous granules and a broadened apical surface in these cells. These ultrastructural characteristics are similar to those of SPEM cells observed in *H. felis*-infected C57BL/6 mice (Wang (1998)). All of these findings indicate that the SPEM lineage is not directly derived from a normal gastric lineage. Rather it appears to represent a metaplastic lineage and is differentiable from both normal mucous neck cells and the goblet cell-containing type metaplasia previously associated with chronic *H. pylori* infection and atrophic gastritis (Dixon, et al. (1996)).

As noted above, the SPEM lineage was observed in apposition with both dysplastic lineages as well as adenocarcinoma. hSP staining was observed in both SPEM as well as in contiguous regions of dysplasia in 49% of resection samples. Immunoreactivity was detectable in a region of adenocarcinoma adjacent to the hSP-immunoreactive cells. At higher magnification, dysplastic epithelial cells appear to be contiguous with SPEM cell-containing glands. Importantly, however, in 59% of the resections, hSP immunoreactivity was present in cells within regions of severe dysplasia or carcinoma in situ. In several cases regions of SP-expressing dysplastic cells were noted extending from regions of SPEM lineage. While regions containing the SPEM lineage did not show significant labelling with Ki-67 and PCNA antibodies, the dysplastic areas showed prominent nuclear labelling in addition to characteristic changes in cell morphology. These results indicate that the SPEM lineage may represent a metaplastic precursor for the development of dysplasia and adenocarcinoma.

Previous investigations have focused on the association of Type III intestinal metaplasia with the development of adenocarcinoma. Despite this association, it is less clear that neoplastic cells actually arise from areas in goblet-cell containing intestinal metaplasia. Of note, while intestinal metaplasia and foveolar hyperplasia are often conspicuous in atrophic gastritis in association with *H. pylori* infection, gastric adenocarcinomas usually develop deep in the glands as nodular lesions that underlie the regions of intestinal metaplasia or foveolar hyperplasia. The identification of the SPEM lineage supports the proposal that this metaplastic candidate precursor is located in proximity with the putative site of neoplastic transition.

It is not clear whether hSP itself might contribute to the development of adenocarcinoma. hSP has generally been associated with cytoprotection in the gastric mucosa (McKenzie, et al., (1997); Tanaka, et al. *Am. J. Physiol*. 272, G1473–G1780 (1997); Babyatsky, et al. *Gastroenterology*. 110, 489–497 (1996)). Homologous deletion of the gene for the gastric surface cell trefoil protein pS2 leads to the development of intramucosal carcinomas (Lefebvre, et al. *Science* 274, 259–262 (1996)), however the lineage responsible for these lesions is unclear. It is more likely that the expression of SP is a functional marker of this metaplastic lineage with Brunner's gland morphology. A metaplasia with Brunner's gland morphology expressing hSP has been associated with acute and chronic injury of the gastrointestinal mucosae (Wright, et al. *Nature*. 343, 82–85 (1990); Ahnen, et al. *J. Pathol*. 173, 317–326 (1994)). Nevertheless, the ulcer-associated cell lineage (UACL) appears to constitute a separate entity, since SPEM does not express ITF. Nevertheless, one can not rule out that SPEM might evolve from UACL in the gastric mucosa.

The presence of a well differentiated metaplastic lesion as a precursor of adenocarcinoma is not without precedence. Esophageal adenocarcinoma develops from dysplastic transition within the metaplastic columnar Barrett's epithelium in the distal esophagus (Reid, et at. *Gasroenterology* 102, 1212–1219 (1992); Miros, et al *Gut* 32, 1441–1446 (1991)). As with the SPEM lineage in the stomach, the Barrett's epithelium shows low proliferative indices. Dysplasia and adenocarcinoma only develop in a minority (10–15%) of patients. These studies indicate that, while the SPEM lineage is commonly associated with fundic *H. pylori* gastritis, only a minority of patients will progress to dysplasia and adenocarcinoma. It is therefore likely that further events must occur to elicit the development of the neoplastic transition. Thus, as recognition and monitoring of Barrett's epithelium is the mainstay of surveillance for the development of esophageal adenocarcinoma (Robertson, et at, M. Br. J. Surg. 75, 760–763 (1988)), so surveillance of patients at risk for gastric adenocarcinoma should focus attention on this metaplastic precursor lineage expressing SP.

In summary, these data support the hypothesis that the SPEM lineage is a link between chronic *H. pylori* gastritis and dysplasia leading to gastric adenocarcinoma.

We claim:

1. A kit for screening for gastric adenocarcinoma in a gastric tissue sample comprising antibodies to spasmolytic peptide to detect Spasmolytic Polypeptide Expressing Metaplasia (SPEM) cells having Brunner's gland morphology, and at least one positive control sample comprising isolated SPEM cells having Brunner's gland morphology in apposition with gastric adenocarcinoma cells.

2. The kit of claim 1 wherein said antibodies to spasmolytic peptide are directly or indirectly labeled.

3. The kit of claim 2 wherein said labeled antibodies to spasmolytic peptide are directly or indirectly labeled with a reagent selected from the group consisting of fluorescent labels, radiolabels, enzyme labels, and dyes.

4. The kit of claim 1 further comprising materials for collecting gastric tissue samples.

5. The kit of 4 further comprising histological stains.

6. The kit of claim 1, further comprising at least one negative control sample comprising histologically normal gastric tissue.

7. The kit of claim 1, further comprising instructions for correlating the levels of SPEM cells in the sample to the likelihood that the sample comprises gastric adenocarcinoma cells.

8. The kit of claim 5, wherein said histological stains comprise a histological stain used to determine whether the sample has gastric adenocarcinoma cells.

9. The kit of claim 5, wherein said histological stains comprise a histological stain used to detect Spasmolytic Polypeptide Expressing Metaplasia (SPEM) cells having Brunner's gland morphology in the sample.

* * * * *

UNITED STATES PATENT AND TRADEMARK OFFICE
CERTIFICATE OF CORRECTION

PATENT NO. : 6,773,890 B2
DATED : August 10, 2004
INVENTOR(S) : James R. Goldenring, P. Henry Schmidt and Jeffrey R. Lee It is certified that error appears in the above-identified patent and that said Letters Patent is hereby corrected as shown below:

Title page,
Item [56], References Cited, OTHER PUBLICATIONS,
"Correa, P.," that portion reading "Cancer Res. 48: 3554-3560 (1988)." should read
-- Cancer Res. 48:3554-3560 (1998). --
"DHI Conference on H pylori," reference, that portion reading "DHI Conference on H. pylori, Gasroenterology 113:S4-S8" should read -- DHI Conference on H pylori, Gastroenterology 113:S4-S8 --
"Konturek, et al.," reference, that portion reading "Konturek, et al., "Activationof genes for spasmolytic pep-" should read -- Konturek, et al. "Activation of genes for spasmolytic pep- --
"Robertson et al.," reference, that portion reading "Robertson, et al., "Values of endoscopic surveillance in the" should read -- Robertson, et al., "Value of endoscopic surveillance in the --

Column 1,
Line 24, that portion reading "followed with endoscopies in rule out future developments." should read -- followed with endoscopies to rule out furture developments. --

Column 4,
Line 42, that portion reading "110, 155-166(1996))." should read -- 110, 155-166 (1996)). --

Column 5,
Line 56, that portion reading "chromogen substrate (Vector-Laboratories, Burlingame," should read -- chromogen substrate (Vector Laboratories, Burlingame, --
Line 59, that portion reading "antibodies against the HIK-ATPase (1:5000, the gift of Dr." should read -- antibodies against the H/K-ATPase 1:5000, the gift of Dr. --

Column 8,
Line 36, that portion reading "in the distal esophagus (Reid, et al. Gasroenterology 102," should read -- in the distal esophagus (Reid, et al., Gastroenterology 102. --

UNITED STATES PATENT AND TRADEMARK OFFICE
CERTIFICATE OF CORRECTION

PATENT NO. : 6,773,890 B2
DATED : August 10, 2004
INVENTOR(S) : James R. Goldenring, P. Henry Schmidt and Jeffrey R. Lee It is certified that error appears in the above-identified patent and that said Letters Patent is hereby corrected as shown below:

Column 8 (cont'd),
Line 48, that portion reading "esophageal adenocarcinoma (Robertson, et al, M. Br. J." should read -- esophageal adenocarcinoma (Robertson, et al., M. Br. J. --

Signed and Sealed this

First Day of March, 2005

JON W. DUDAS
*Director of the United States Patent and Trademark Office*